United States Patent [19]

Park et al.

[11] Patent Number: 5,113,025
[45] Date of Patent: May 12, 1992

[54] SELECTIVE REDUCING AGENTS

[75] Inventors: Won S. Park; Everett M. Marlett, both of Baton Rouge, La.

[73] Assignee: Ethyl Corporation, Richmond, Va.

[21] Appl. No.: 664,637

[22] Filed: Mar. 5, 1991

Related U.S. Application Data

[63] Continuation-in-part of Ser. No. 416,148, Oct. 2, 1989, abandoned, which is a continuation-in-part of Ser. No. 337,085, Apr. 12, 1989, abandoned.

[51] Int. Cl.$^5$ .................. C07C 29/136; C07C 29/159; C07C 209/048
[52] U.S. Cl. .................................... 568/814; 564/375; 564/385; 564/415; 564/416; 564/812; 564/841; 564/864
[58] Field of Search ............... 568/814, 841, 862, 864, 568/880, 881, 840, 814, 816, 820; 564/472, 375, 385, 415, 416

*Primary Examiner*—Werren B. Lone
*Attorney, Agent, or Firm*—Richard J. Hammond

[57] ABSTRACT

A process for selective reduction is provided wherein an organic compound containing a reducible group such as acid, acid chloride, ester, aldehyde, ketone, epoxide, amide, oxime, imine, nitrile, or the like, is reacted with a tertiary amine alane such that an alcohol or an amine is produced, substantially without reduction of another group in the molecule such as a halogen-containing functionality, nitro group, or double bond.

15 Claims, No Drawings

SELECTIVE REDUCING AGENTS

REFERENCE TO RELATED APPLICATION

This application is a continuation-in-part of co-pending application Ser. No. 416,148, filed Oct. 2, 1989 now abandoned (which was a continuation-in-part of co-pending application Ser. No. 337,085 filed Apr. 12, 1989) now abandoned.

TECHNICAL FIELD

This invention relates to the use of selective reducing agents in the chemical reduction of certain types of reducible organic compounds.

BACKGROUND

Prior co-pending application Ser. No. 337,085, filed Apr. 12, 1989 and application Ser. No. 416,148 filed Oct. 2, 1989, disclose the preparation of N,N-dimethylethylamine alane and N-methylpyrrolidine alane by extraction of $AlH_3$ from lithium aluminum tetrahydride by the appropriate tertiary amine. Use of amine alanes as reducing agents is also disclosed therein.

Amine alanes have also been produced by the reaction of alkali metal aluminum tetrahydride, silicon tetrachloride, and tertiary amine; by the reaction of alkali metal aluminum tetrahydride, tertiary amine, and hydrochloric acid or an analog; and by the reaction of alkali metal aluminum tetrahalide, alkali metal aluminum tetrahydride, and tertiary amine. These methods are disclosed in the following U.S. Patents, respectively: Marlett and Frey, U.S. Pat. No. 4,757,154; Marlett, U.S. Pat. No. 4,748,260; and Marlett, U.S. Pat. No. 4,665,207. These patents also make reference to Marlett, U.S. Pat. No. 4,474,743, and to references cited therein, which set forth several other general methods for preparation of amine alanes:

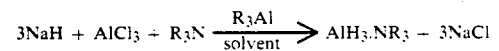  (1)

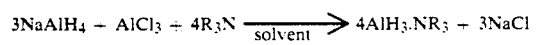  (2)

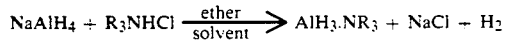  (3)

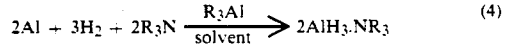  (4)

Also, $LiAlH_4$ can be reacted with a trialkyl amine. HCl complex to precipitate LiCl and form $AlH_3.NR_3$ where R is alkyl.

U.S. Pat. No. 4,474,743 also states that: "Alane, that is, aluminum trihydride or $AlH_3$, has in the past been produced from the reaction of $LiAlH_4$ and $AlCl_3$ in ethers. Also known is the production of an alane-dimethyl ether solution from the reaction of LiH and $AlCl_3$ in dimethyl ether, catalyzed by $NaAlH_4$."

Brown and Yoon, J. Am. Chem. Soc. 1966, 88, 1464–1472, have prepared alane in tetrahydrofuran, that is, $AlH_3$ in THF, by reaction of exact stoichiometric quantities of lithium aluminum tetrahydride and 100% sulfuric acid. After about three days, the resulting solution begins to decompose with cleavage of the solvent.

Brown and Yoon, cited above, and Yoon and Brown, J. Am. Chem. Soc. 1968, 90, 2927–2938, have reported the use of this reagent, aluminum hydride in THF, for selective reductions of organic compounds. They made comparisons of this reagent with $LiAlH_4$ and with alkoxy-substituted lithium aluminum hydrides and found "significant differences in reducing characteristics" (Yoon and Brown, p. 2927, column 1).

A selective reduction process is useful in organic synthesis where more than one functional group occurs in a molecule and it is desired to reduce one but not another, for example, to reduce an acid or a nitrile without reducing a nearby halogen-containing functionality or double bond.

THE INVENTION

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl.

Cycloalkyl means cyclic alkyl having 3 to 7 carbon atoms and includes cyclopropyl, cyclobutyl, cyclopentyl, cyclohexyl and cycloheptyl.

Substituted phenyl or naphthyl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Heteroaryl means 5 to 10 membered mono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl.

Substituted heteroaryl means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus.

Haloalkyl means straight or branched chain alkyl having 1 to 10 carbon atoms which is substituted at least one halogen as mentioned above.

Hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1-hydroxy-2-propyl, 2-hydroxypropyl, 2,3-dihydroxypropyl, 1,3-dihydroxy-2-propyl.

Alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, oxyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexylxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexyloxyoctyl and 8-octyloxyoctyl.

Alkylthioalkyl means that the alkylthio moiety and the alkyl moiety each are straight or branched chain ones having 1 to 8 carbon atoms and includes, for example, methylthiomethyl, ethylthiomethyl, propylthiomethyl, isopropylthiomethyl, butylthiomethyl, isobutylthiomethyl, tertiary butylthiomethyl, pentylthiomethyl, hexylthiomethyl, octylthiomethyl, 2-methylthioethyl, 2-ethylthioethyl, 2-butylthioethyl, 2-hexylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 4-butylthiobutyl, 6-methylthiohexyl, 6-ethylthiohexyl, 6-butylthiohexyl, 8-methylthiooctyl, 8-ethylthiooctyl and 8-butylthiooctyl.

Phenylalkyl or naphthylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl, 8-phenyloctyl, and 2-naphthylethyl.

Substituted phenylalkyl or naphthyl alkyl means above-mentioned phenylalkyl or naphthylalkyl which is substituted by at least one substituent selected from the group consisting of halogen, amino, nitro, hydroxy, alkyl, alkoxy and haloalkyl on the phenyl nucleus.

Heteroarylalkyl means that the heteroaryl moiety is 5 to 10 membered mono- or fused-heteroaromatic ring having at least one heteroatom selected from the group consisting of nitrogen, oxygen and sulfur as mentioned above and the alkyl moiety is straight or branched chain alkyl having 1 to 8 carbon atoms, and includes, for example, furfuryl, 3-furylmethyl, 2-thienyl, 3-thienyl, 2-, 3- or 4-pyridylmethyl, pyrazolylmethyl, 1-imidazolylmethyl, pyrimidinylmethyl, benzimidazolylmethyl, 2-(2-furyl)ethyl, 2-(2-thienyl)ethyl, 2-(2-pyridyl)ethyl, 2-(1-imidazolyl)ethyl, 3-(2-furyl)propyl, 3-(2-thienyl)propyl, 3-(2-pyridyl)propyl, 4-(2-furyl)butyl, 4-(2-thienyl)butyl and 4-(2-pyridyl)butyl.

Substituted heteroarylalkyl means that the substituted heteroaryl moiety is 5 to 10 membered mono- or fused-heteroaromatic ring which is substituted by at least one substituent selected from the group consisting of halogen, amino, nitro, hydroxy, alkyl, alkoxy and haloalkyl on the heteroaryl nucleus and which has at least one heteroatom selected from the group consisting of nitrogen, oxygen and sulfur as mentioned above, and that the alkyl moiety is straight or branched chain alkyl having 1 to 8 carbon atoms.

Cycloalkylalkyl means that the cycloalkyl moiety is cyclic alkyl having 3 to 7 carbon atoms and the alkyl moiety is straight or branched chain alkyl having 1 to 8 carbon atoms, and includes, for example: cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl and 6-cyclohexylhexyl.

Acids means aliphatic or aromatic monocarboxylic acids. As such, these aliphatic monocarboxylic acids include those having the carbon atom of a carboxylic acid group attached to the following aliphatic groups: alkyl, cycloalkyl, haloalkyl, hydroxyalkyl, alkoxyalkyl, alkylthioalkyl, phenylalkyl, naphthylalkyl, substituted phenylalkyl, substituted naphthyl alkyl, heteroarylalkyl, substituted heteroarylalkyl and cycloalkylalkyl. The aromatic monocarboxylic acids include those having the carbon atom of the carboxylic acid group attached to the following aromatic groups: phenyl, naphthyl, substituted phenyl, substituted naphthyl, heteroaryl, and substituted heteroaryl.

Esters means the aliphatic or aromatic esters of the above defined aliphatic and aromatic monocarboxylic acids. Thus, the aliphatic esters are the above carboxylic acids that are alkyl, cycloalkyl, haloalkyl, hydroxyalkyl, alkoxyalkyl, alkylthioalkyl, phenylalkyl, naphthylalkyl, substituted phenylalkyl, substituted naphthylalkyl, heteroarylalkyl, substituted heteroarylalkyl and cycloalkylalkyl esters. The aromatic esters are the above carboxylic acids that are phenyl, naphthyl, substituted phenyl, substituted naphthyl, heteroaryl and substituted heteroaryl esters.

The acid chlorides are the acid chloride forms of the above defined carboxylic acids.

Lactones and lactams include the $\beta$ and $\gamma$ lactones and lactams of the above carboxylic acids.

Epoxides are the symmetrical and unsymmetrical epoxides having the above disclosed aliphatic, aromatic or mixed aliphatic and aromatic groups.

Salts of the above carboxylic acids include metallic salts (e.g., sodium salt, potassium salt, calcium salt, magnesium salt or aluminum salt), salts with bases (e.g., salt with triethylamine, diethanolamine, ammonium, guanidine, hydrazine, quinine or cinchonin) or salts with amino acids (e.g., salt with lysine or glutamine).

Aldehydes are the above disclosed carboxylic acids where the carboxylic acid group is transformed into an aldehyde one.

Ketones include the above mentioned aliphatic or aromatic carboxylic acids having the carboxylic acid group transformed into a ketone, with the other valency being occupied by aliphatic or aromatic groups disclosed above.

The nitriles, amides, oximes, imines include the aliphatic and aromatic substituted species of these compounds.

A process has been discovered for the selective reduction of organic compounds, in excellent yields, wherein the selective reducing reagent is stable and is easily prepared and handled.

In accordance with this invention, an organic compound which contains at least one carbon atom having more than one bond to oxygen or nitrogen, or at least one oxygen atom having a single bond to each of two carbons adjacent to each other, and a tertiary amine alane are reacted together such that an alcohol or an amine is produced.

In one embodiment of this invention, a tertiary amine alane is reacted with an organic compound selected from the class consisting of acids, esters, acid chlorides, aldehydes, ketones and epoxides, such that an alcohol is produced.

In another embodiment of this invention, a tertiary amine alane is reacted with an organic compound selected from the class consisting of amides, oximes, imines, and nitriles, such that an amine is produced.

In a preferred embodiment of this invention, the reaction is conducted in a liquid medium which comprises one or more ethers, one or more hydrocarbons, or a mixture thereof. In a highly preferred embodiment, the liquid medium is aromatic hydrocarbon containing a reaction-enhancing quantity of ether.

Organic compounds which are suitable for the practice of this invention are those which contain reducible groups wherein at least one carbon atom has more than one bond to oxygen or nitrogen, or wherein at least one oxygen atom has a single bond to each of two carbons adjacent to each other. Thus, acids and their salts, esters, and acid chlorides are all suitable, as are aldehydes, ketones, lactones, and epoxides. The expected product of reduction of each of these substances is an alcohol. Also suitable are nitriles, amides, oximes, imines, lactams, and similar compounds. The expected product of reduction of each of these substances is an amine.

Most other types of groups which might be present in the molecule are reduced very much more slowly in the process of this invention, thus allowing selective reduction. Reduction of the recited suitable groups occurs in high yields in short enough times that substantially none of the other groups are reduced. This invention thus provides a process whereby functional groups such as halides, nitro groups, double bonds, and similar functions remain unreduced in a molecule while the previously recited reducible functional groups are selectively reduced.

Amine alanes may be prepared by any convenient method disclosed above. Any amine alane may be used which is soluble in the liquid medium of the reaction. Suitable amines for preparing the amine alane reactant can be alkyl, cycloalkyl, alkenyl, aryl, and aralkyl amines, including monoamines, diamines, and polyamines. Examples of such amines are: N,N-diphenylmethylamine, phenylmethylethylamine, tricyclohexylamine, N,N,N',N'-tetramethylethylenediamine, quinuclidine (1-azabicyclo[2.2.2]octane), N,N,N',N'-tetramethyldiaminomethane, and the like. Preferred amines are aliphatic tertiary amines, such as trimethylamine, triethylamine, triisopropylamine, N-methylpyrrolidine, N,N-dimethylethylamine, N,N-diethylmethylamine, N,N-dimethylpropylamine, tri-n-butylamine, tri-sec-butylamine, N,N-di-n-butylpentylamine, n-butyl-n-octyl-sec-butylamine, tripentylamine, trihexylamine, trihexenylamine, trioctadecylamine, N,N-didecenylpentylamine, tridecenylamine, and the like, as well as mixtures thereof. Most preferred are amine alanes which are conveniently and inexpensively prepared. Especially preferred in the process of this invention are amine alanes having eight or fewer carbon atoms. Triethylamine alane is preferred; it is conveniently prepared, as set forth in the examples of U.S. Pat. No. 4,474,743. Most highly preferred are N,N-dimethylethylamine alane and N-methylpyrrolidine alane, which are easily prepared by extraction using the appropriate amine and lithium aluminum tetrahydride, as disclosed in prior co-pending application Ser. No. 337,085, filed Apr. 12, 1989. These amine alanes are not only easily prepared but are also very stable. They may be stored in hydrocarbon solvent at room temperature in closed containers for six months or more without decomposition.

In determining molar proportions of reactants to be used in the process of this invention, it must be kept in mind that one mole of amine alane provides three moles or three equivalents of hydrogen as a reducing agent, whereas one mole of organic compound to be reduced requires an amount of hydrogen which depends on the particular compound undergoing the process of this invention. Anyone skilled in the art would know the number of hydrogens per mole required to reduce a given organic compound to the alcohol (in the alkoxide form) or to the amine. The preferred molar proportions are from about equivalent quantities up to about 100% excess (equivalents) of hydrogen. From about equivalent quantities to about 50% excess of hydrogen is more preferred, and from about equivalent quantities to about 33% excess is most preferred.

The process of this invention is preferably conducted in a liquid medium. In addition to aiding in mixing and transferring reactants, the use of a liquid diluent also aids in controlling rates of reactions. Other considerations are solubility of reactants and ease of separating the product, as well as expense and ease of handling the liquid medium. The suitability of a given liquid might vary somewhat according to the nature of the organic compound to be reduced in the process of this invention, but the suitability of such liquid can easily be determined by means of a few simple tests by one skilled in the art.

Tertiary amines, hydrocarbons, ethers, or mixtures of these can be used as liquid media for the process of this invention. Any amine suitable for preparing the amine alane, as recited above, is also suitable for use as a liquid reaction medium, provided that it is liquid under the conditions of the reaction. However, ethers and hydrocarbons are preferred.

Various ethers may be used to comprise the liquid reaction medium, either singly or in admixture, for example, diethyl ether, dipropyl ether, di-isopropyl ether, ethyl propyl ether, methyl propyl ether, dibutyl ether, ethyl butyl ether, polyethers such as glyme (dimethoxyethane, or the dimethyl ether of ethylene glycol), diglyme (the dimethyl ether of diethylene glycol), triglyme (the dimethyl ether of triethylene glycol), tetraglyme (the dimethyl ether of tetraethylene glycol), dimethoxypropane, and the like, as well as 1,4-dioxane, 1,3-dioxolane, tetrahydrofuran, 2-methyltetrahydrofuran, 3-methyltetrahydrofuran, 2,5-dimethyltetrahydrofuran, and similar substances. Polyethers are preferred, particularly dimethoxyethane and diglyme; tetrahydrofuran is most highly preferred.

Alkanes such as pentane, hexane, heptane, octane, nonane, decane, undecane, dodecane, and the like can be used. Aromatic hydrocarbons are particularly preferred, especially mononuclear aromatic hydrocarbons. Among those which can be used, either singly or in admixture, are benzene, toluene, ethylbenzene, propylbenzene, isopropylbenzene, butyl benzenes, xylenes, mesitylene, higher alkyl and dialkyl benzenes such as 1,2-diethylbenzene, 1,3-diethylbenzene, 1,4-diethylbenzene, 1,3-dipropylbenzene, 3-propyltoluene, 4-ethyltoluene, 4-propyltoluene, 4-butyltoluene, trialkylbenzenes, 1-methylnaphthalene, 1,2,3,4-tetrahydronaphthalene, and similar compounds. One convenient solvent is the commercially available mixture of benzene, toluene, and xylene, commonly known as BTX. Mixtures of hydrocarbons predominating in aromatic components but with minor amounts of aliphatic or cycloaliphatic components may also be used. Mixtures of ethers and hydrocarbons may also be used. Most highly preferred is aromatic hydrocarbon containing a reaction-enhancing quantity of ether.

While it is preferable to prepare and store the amine alane reactant in a hydrocarbon medium, for example, in toluene, it is found that ether is desirable as a reaction-enhancing component in the reaction medium. While this invention is not limited by any theoretical consideration whatsoever, it appears that a more polar reaction medium is more advantageous due to the polar nature of the reactant. From about 10% to about 95% ether is preferable and from about 50% to about 95% ether is more preferable.

One skilled in the art can easily choose an amount of liquid medium for the conduct of the reaction. It is preferable, though not essential, to conduct the reaction in one phase, i.e., in solution. There is no real upper limit to the amount of solvent employed, but a skilled practitioner will not use dilutions so great as unduly to inhibit the rate of reaction or to hamper the recovery of the product. The lower limit is preferably determined by the solubility of the reactants, which, of course, will vary according to the particular solvent and reactants used in the practice of this invention. More preferably the amount of liquid used will make the concentration of the reducible organic reactant from about 0.01 molar to about 1 molar (or to about the solubility limit if it is less soluble). In the most preferred amount, the organic reactant will be from about 0.1 molar to about 0.5 molar. The concentration of the amine alane reactant will most preferably be determined according to the stoichiometric ratios discussed above.

Preferably, the reaction is conducted under substantially anhydrous conditions, but trace amounts of moisture as might normally be found in industrial reagents used for similar purposes, are acceptable. The reaction is preferably conducted in an inert atmosphere.

The temperature at which the practice of this invention is conducted may be varied. Depending on the nature of the organic compound to be reduced and the concentration conditions, one skilled in the art may easily adjust the temperature appropriately. Temperatures from somewhat below 0° C. to about 80° C. are suitable, and a temperature of from about 0° C. to about 35° C. is preferred.

The pressure under which the reaction is conducted is not critical, and may be subatmospheric, atmospheric, or superatmospheric. Satisfactory pressures are from about atmospheric up to about 10 atmospheres. The reaction is preferably conducted at atmospheric or ambient pressure; highly preferred is a pressure in the closed reaction vessel which is slightly above ambient pressure.

The time of the reaction, of course, depends on the other variables chosen. In general the reaction will be complete in from a few minutes to about eight hours, most usually from about 0.5 hours to about three hours.

EXAMPLES

The following examples illustrate the practice of this invention, but are not intended to limit the spirit and scope of it.

EXAMPLE 1

The following procedure for the reduction of ethyl 3-chloropropionate with N,N-dimethylethylamine alane, $AlH_3 \cdot NMe_2Et$, is representative of the selective reduction of the organic compounds examined. The reduction was carried out under a nitrogen atmosphere. The amine alane solution in toluene (11.4 mL, 0.88M) was introduced to a 100 mL round-bottomed flask containing tetrahydrofuran (THF, 20.3 mL) via a hypodermic syringe. The mixture was cooled to 0° C. The ester, contained in dry THF (8.3 mL, 1.2M) previously cooled to 0° C., was added to the reagent solution with stirring at 0° C. (to give a final volume of 40.0 mL). Formation of a white precipitate was observed immediately. After 15 minutes, the reaction mixture was hydrolyzed with 6 mL of THF-$H_2O$ (1:1 mixture). An amount of 1-octanol (0.640 g, 4.91 mmoles) was added as an internal standard. The organic layer was separated and dried over $MgSO_4$. Analysis by gas chromatography (GC) using a 60-meter FFAP capillary column gave 9.91 mmoles of 3-chloro-1-propanol for a 99% yield. The identity of the product was confirmed upon analysis by proton nuclear magnetic resonance spectroscopy ($^1H$ NMR).

EXAMPLES 2-5

The reactions of the following examples were each conducted in a THF-toluene medium wherein the concentration of the organic reactant was 0.25 M. The mole ratio of N,N-dimethylethylamine alane reactant to organic reactant was 1.33:1, except for the cases of ethyl 3-chloropropionate and p-nitrobenzoyl chloride, where it was 1:1. The yield of benzylamine was determined by titration. N,N-dimethylbenzylamine and p-nitrobenzylalcohol yields were determined by isolation, and the 1-hexanol yield was determined by $^1H$ NMR with methylenecyclohexane as an internal standard.

| Example | Organic Reactant | Temp °C. | Time hr. | Product | Yield % |
|---|---|---|---|---|---|
| 1 | ethyl 3-chloropropionate | 0 | 0.25 | 3-chloro-1-propanol | 99 |
| 2 | caproic acid | 0 | 3.0 | 1-hexanol | 99 |
| 3 | p-nitrobenzoyl chloride | 0 | 0.5 | p-nitrobenzylalcohol | 90 |
| 4 | N,N-dimethylbenzamide | 25 | 0.5 | N,N-dimethylbenzylamine | 98 |
| 5 | benzonitrile | 25 | 1.0 | benzylamine | 98 |

What is claimed is:

1. In a process for preparing alcohols or amines by selective reduction which process comprises reacting a reducible compound that is an aliphatic monocarboxylic acid having the aliphatic group selected from the group consisting essentially of alkyl, cycloalkyl, haloalkyl, hydroxyalkyl, alkoxyalkyl, alkylthioalkyl, phenylalkyl, naphthylalkyl, substituted phenylalkyl, substituted naphthylalkyl, heteroarylalkyl, substituted heteroarylalkyl and cycloalkylalkyl;

aromatic monocarboxylic acid having the carbon atom of the carboxylic acid group attached to an aromatic group selected from the group consisting essentially of phenyl, naphthyl, substituted phenyl, substituted naphthyl, heteroaryl, and substituted heteroaryl;

the aliphatic esters of said aliphatic or aromatic monocarboxylic acid, the ester group selected from the group consisting essentially of alkyl, cycloalkyl, haloalkyl, hydroxyalkyl, alkoxyalkyl, alkylthioalkyl, phenylalkyl, naphthylalkyl, substituted phenylalkyl, substituted naphthylalkyl, heteroarylalkyl, substituted heteroarylalkyl and cycloalkylalkyl;

the aromatic esters of said aliphatic or aromatic monocarboxylic acid, the ester group selected from the group consisting essentially of phenyl, naphthyl, substituted phenyl, substituted naphthyl, heteroaryl and substituted heteroaryl esters;

a compound where the carboxylic acid group of said aliphatic monocarboxylic acid or said aromatic monocarboxylic acid is replaced with a functional group selected from the group consisting essentially of acid chloride, amide, aldehyde, nitrile, β-lactone, γ-lactone, symmetrical epoxide, unsymmetrical epoxide and ketone wherein the other valency of said ketone is an aliphatic group or an aromatic group as previously defined;

an aliphatic monocarboxylic acid salt selected from the group consisting essentially of the metallic salts, salts with organic bases and salts with amino acids;

or an aromatic monocarboxylic acid salt, said salt selected from the group consisting essentially of the metallic salt, salt with an organic base and salt with an amino acid said reducible compound also containing at least one other reducible functional group or functionality selected from the group consisting essentially of halide, nitro and double bond, the improvement comprising treating said reducible compound with a tertiary amine alane having from 3 to about 8 carbon atoms.

2. A process of claim 1 wherein said amine alane is N,N-dimethylethylamine alane.

3. A process of claim 1 wherein said amine alane is N-methylpyrrolidine alane.

4. A process of claim 1 wherein said amine alane is triethylamine alane.

5. A process of claim 1 conducted in a reaction medium which is predominantly ether.

6. A process of claim 5 wherein said ether is tetrahydrofuran.

7. A process of claim 1 conducted in a reaction medium which is predominantly hydrocarbon.

8. A process of claim 7 wherein said hydrocarbon is aromatic.

9. A process of claim 8 wherein said hydrocarbon is toluene.

10. A process of claim 7 wherein said hydrocarbon contains a reaction-enhancing quantity of ether.

11. A process of claim 1 wherein said other reducible functional group or functionality is a halide.

12. A process of claim 1 wherein said other reducible functional group or functionality is a nitro group.

13. A process of claim 1 wherein said other reducible functional group or functionality is a double bond.

14. A process of claim 1 conducted in a reaction medium which is predominantly ether.

15. A process of claim 14 wherein said ether is tetrahydrofuran.

* * * * *